(12) United States Patent
Warner et al.

(10) Patent No.: US 7,700,801 B2
(45) Date of Patent: Apr. 20, 2010

(54) CO-PRODUCTION OF VINYL ACETATE AND ETHYL ACETATE

(75) Inventors: R. Jay Warner, Houston, TX (US); J. Alfonso Torres, Corpus Christi, TX (US)

(73) Assignee: Celanese International Corporation, Dallas, TX (US)

( * ) Notice: Subject to any disclaimer, the term of this patent is extended or adjusted under 35 U.S.C. 154(b) by 1526 days.

(21) Appl. No.: 10/988,683

(22) Filed: Nov. 15, 2004

(65) Prior Publication Data

US 2006/0106246 A1    May 18, 2006

(51) Int. Cl.
C07C 67/00    (2006.01)

(52) U.S. Cl. ..................................................... 560/241

(58) Field of Classification Search ................ None
See application file for complete search history.

(56) References Cited

U.S. PATENT DOCUMENTS

| | | | | |
|---|---|---|---|---|
| 4,337,329 A * | 6/1982 | Kubo et al. | ................. | 525/339 |
| 4,365,084 A | 12/1982 | Young | ........................ | 560/247 |
| 4,405,808 A | 9/1983 | Nakajima et al. | ........... | 560/247 |
| 4,645,849 A | 2/1987 | Lewis | ........................ | 556/16 |
| 4,818,347 A | 4/1989 | Roscher et al. | ............... | 203/42 |
| 4,886,905 A * | 12/1989 | Larkins, Jr. | .................. | 560/265 |
| 4,892,928 A * | 1/1990 | Hoxmeier | .................... | 525/338 |
| 4,897,161 A * | 1/1990 | Berg et al. | ................... | 203/51 |
| 5,066,365 A | 11/1991 | Roscher et al. | ............... | 203/42 |
| 5,225,388 A | 7/1993 | Wunder et al. | ............... | 502/170 |
| 5,821,384 A | 10/1998 | Zoeller et al. | ............... | 560/231 |
| 5,936,117 A | 8/1999 | Zoeller et al. | ............... | 560/233 |
| 6,187,949 B1 | 2/2001 | Froom et al. | ................. | 560/247 |
| 6,410,817 B1 | 6/2002 | Colling et al. | .............. | 585/866 |
| 6,420,595 B1 * | 7/2002 | Hallinan et al. | ............. | 560/245 |
| 6,476,261 B2 * | 11/2002 | Ellis et al. | .................... | 562/606 |
| 6,620,965 B1 | 9/2003 | Adams et al. | ............... | 560/245 |
| 6,663,692 B2 | 12/2003 | de Poitiers et al. | ............ | 95/237 |
| 6,696,596 B1 | 2/2004 | Herzog et al. | ............... | 560/245 |
| 6,727,380 B2 | 4/2004 | Ellis et al. | .................... | 560/241 |
| 6,936,730 B1 * | 8/2005 | Ohga et al. | ................. | 560/128 |
| 7,262,322 B2 * | 8/2007 | Ferguson et al. | ............ | 560/241 |

FOREIGN PATENT DOCUMENTS

RO    103511 A  *  1/1992
WO    WO 03/011809    2/2003

* cited by examiner

*Primary Examiner*—Jafar Parsa
*Assistant Examiner*—Chukwuma O Nwaonicha (57) ABSTRACT

A method of co-producing vinyl acetate and ethyl acetate includes: (a) reacting ethylene, acetic acid and oxygen to form vinyl acetate and at least a minor amount of ethyl acetate; (b) providing a crude product stream containing the vinyl acetate and ethyl acetate of step (a) and acetic acid to a distillation tower; (c) separating the crude product stream into: (i) a vinyl acetate product stream enriched in vinyl acetate with respect to the crude product stream; (ii) an acid recycle stream enriched in acetic acid with respect to the crude product stream; (iii) a mixed sidestream containing vinyl acetate and ethyl acetate, the mixed sidestream being enriched in ethyl acetate with respect to the vinyl acetate product stream; and (d) hydrogenating vinyl acetate in the mixed sidestream to provide an ethyl acetate product stream.

15 Claims, 3 Drawing Sheets

CO-PRODUCTION OF VINYL ACETATE AND ETHYL ACETATE

TECHNICAL FIELD

The present invention is directed to a co-production process and apparatus for concurrently producing vinyl acetate and ethyl acetate. The process reduces overall capital costs and allows for higher azeotrope column throughputs. Vinyl acetate in an ethyl acetate-enriched sidestream from a vinyl acetate azeotrope column is hydrogenated to ethyl acetate.

BACKGROUND

The production of vinyl acetate is well known. The preferred method is by way of reacting of acetic acid (I) and ethylene (II) in the presence of oxygen to produce the vinyl acetic monomer (III):

Water and by-products are also produced, notably ethyl acetate. U.S. Pat. No. 6,420,595, entitled "Process Control for Vinyl Acetate Manufacturing" of Hallinan et al., provides an overview of the commercially preferred vapor-phase oxidation process wherein the crude product is fed to an azeotrope column and separated into a product stream and a waste ethyl acetate stream. Further details of this process appear in other patents, such as U.S. Pat. No. 6,410,817 to Colling and U.S. Pat. No. 6,696,596 to Herzog et al.

Alternatively, a liquid phase or mixed phase process can be used as is seen in U.S. Pat. No. 6,620,965 to Adams et al.

U.S. Pat. No. 5,225,388, entitled "Method for Making a Catalyst" of Wunder et al., relates to a process for the preparation of vinyl acetate from ethylene, acetic acid and oxygen or oxygen-containing gases on a catalyst which contains palladium and/or its compounds and, if desired, gold and/or gold compounds and alkali metal compounds as activators and, if desired, additionally cadmium compounds on a support which is composed of $SiO_2$ or a $SiO_2$—$Al_2O_3$ mixture having a surface area of 50-250 $m^2$/g, a pore volume of 0.4-1.2 ml/g and a particle size of 4 to 9 mm, which comprises compressing the support particles with the aid of an Li, Mg, Al, Zn or Mn salt of a $C_2$-$C_{20}$ carboxylic acid or a mixture of such salts as binder.

U.S. Pat. No. 4,897,161, entitled "Separation of Vinyl Acetate from Ethyl Acetate by Extractive Distillation" of Berg et al., describes a process whereby vinyl acetate can be readily separated from ethyl acetate by means of extractive distillation using certain glycols or glycol ethers. Typical effective agents are 2-methyl-2,4-pentanediol, 1,3-butanediol, ethylene glycol methyl ether and diethylene glycol ethyl ether.

U.S. Pat. No. 4,818,347, entitled "Process for the Isolation of Vinyl Acetate" of Roscher et al., relates to a process for the isolation of vinyl acetate from a gas mixture containing vinyl acetate, ethyl acetate, water and carbon dioxide formed in the reaction of ethylene with acetic acid and oxygen in the gas phase over catalysts containing palladium or palladium compounds. The gas mixture leaving the reaction zone is passed into a distillation column and the gas mixture leaving the top thereof is cooled. The gas, which is not condensed during the cooling, is washed with acetic acid in a washing column, an acetic acid solution containing vinyl acetate being obtained. The bottom product from the distillation column is passed to a second distillation column and a side stream containing ethyl acetate is removed from an enrichment zone above the bottom thereof, all or some of the bottom product from the second distillation column, which product chiefly consists of acetic acid, being used for the wash in the washing column. The top vapor of the second distillation column is cooled. A portion of the organic phase of the condensate thereby formed is passed, together with the acetic acid solution obtained as the bottom product in the washing column, into a third distillation column, which may have an intermediate tray. The bottom product of the third distillation column is passed into a fourth distillation column. Pure vinyl acetate is removed at the top of the fourth distillation column.

Another process for the isolation of vinyl acetate by distillation is described in U.S. Pat. No. 5,066,365 entitled "Process for the Isolation of Vinyl Acetate by Distillation" of Roscher et al. This process for the isolation of vinyl acetate involves not combining the bottom product of the recycled gas washings with the water-saturated vinyl acetate but rather introducing it to further multiple distillation columns from the gas mixture formed in the reaction of ethylene with acetic acid and oxygen over catalysts containing palladium or palladium compounds in the gas phase.

A more exotic process is seen in U.S. Pat. No. 5,821,384, entitled "Process for Generating Vinyl Carboxylate Esters" of Zoeller et al., which describes a process for producing a vinyl carboxylate ester from a carbonyl compound and a carboxylic acid anhydride. The process comprises feeding a carboxylic acid anhydride to the middle portion of a reactive distillation column (RDC) while feeding a carbonyl compound to the lower section of the RDC and removing a product comprising the vinyl carboxylate ester. A carboxylic acid co-product corresponding to the anhydride reactant may be removed from the upper section of the RDC with the vinyl carboxylate ester, or from the upper section of the RDC as a separate side draw. Unreacted carbonyl may be removed from the RDC from the top along with the vinyl carboxylate ester or separately removed and recycled to the bottom portion of the RDC. Unreacted anhydride and an alkylidene dicarboxylate may be removed from the base of the RDC and recycled to the middle portion of the RDC. The product vinyl carboxylate may be further purified in one or two additional distillation vessels.

Ethyl acetate may be prepared by a variety of processes, including by way of direct addition of acetic acid with ethylene, or by way of oxidative acetoxylation of ethylene followed by hydrogenation of vinyl acetate or by way of esterification of acetic acid with ethanol. The process of preparing ethyl acetate by direct addition is relatively expensive because of the equipment required for the process. These processes are represented as follows:

Direct (Michael) Addition:

Oxidative Acetoxylation/Hydrogenation:

Esterification:

Other processes include those which use acetaldehyde or ethanol as starting materials.

The synthesis of lower aliphatic esters using heteropolyacids with an aldehyde-free product stream is described in U.S. Pat. No. 6,187,949 entitled "Synthesis of Lower Aliphatic Esters Using Heterpolyacids with an Aldehyde-Free Product Stream" of Froom et al. This invention describes a process for the production of lower aliphatic esters by bringing together in an addition reaction a lower olefin and a saturated, lower aliphatic, mono-carboxylic acid in the vapor phase into contact with a heteropolyacid catalyst. The reactant olefin and acids and any recycled feeds are rendered substantially free of aldehyde impurities prior to being brought into contact with the heteropolyacid catalyst. Acetaldehyde is a catalyst poison and removal of these from the feeds prolongs life and activity of the heteropolyacid catalyst.

U.S. Pat. No. 6,727,380 entitled "Oxidation Process for the Production of Alkenes and Carboxylic Acids" of Ellis et al., U.S. Pat. No. 6,548,697 entitled "Oxidation Process for the Production of Alkenes and Carboxylic Acids" of Ellis et al., and U.S. Pat. No. 6,476,261 entitled "Oxidation Process for the Production of Alkenes and Carboxylic Acids" of Ellis et al., describe a process for the oxidation of a $C_2$ to $C_4$ alkane to produce the corresponding alkene and carboxylic acid and further to integrated processes in which a portion of the produced alkene and carboxylic acid are used as reactants, in a second reaction zone, for the production of alkyl carboxylates.

U.S. Pat. No. 5,936,117, entitled "Carbonylation of Olefins" of Zoeller et al., describes a process for the preparation of aliphatic carbonyl compounds selected from aliphatic carboxylic acids, alkyl esters of aliphatic carboxylic acids and anhydrides of aliphatic carboxylic acids by the carbonylation of olefins in the presence of a catalyst system comprising (1) a primary component selected from at least one Group 6 metal, i.e., chromium, molybdenum, and/or tungsten and (2) a secondary component selected from at least one of certain halides and tertiary and quaternary compounds of a Group 15 element, i.e., nitrogen, phosphorus and/or arsenic. The process can be carried out at moderate carbonylation conditions without the necessity of using an expensive noble metal catalyst, volatile, toxic materials such as nickel tetracarbonyl, formic acid or a formate ester. U.S. Pat. No. 4,405,808 entitled "Process for Preparing Acetic Acid Esters" of Nakajima et al. describes a process for preparing acetic acid esters by reacting acetic acid with an aliphatic lower olefin in vapor phase in the presence of steam and a catalyst selected from aromatic disulfonic acids and their esters. The high activity of the catalyst can be maintained and the product is obtained in a high space time yield by the presence of steam in the reaction. The effect of maintaining the high activity can be further increased by using silica treated with a strong acid as a carrier.

U.S. Pat. No. 4,365,084, entitled "Preparation of Alkyl Carboxylates" of Young, describes a method for the preparation of alkyl carboxylate compounds, and especially α-methylalkyl carboxylate compounds, by reaction of an olefin and a carboxylic acid compound in the presence of a particular type of zeolite catalyst. The zeolites are characterized by a silica to alumina mole ratio of at least 12 and a constraint index of 1 to 12.

In connection with the production of either vinyl acetate or ethyl acetate a large portion of the capital and operating expense is due to purification requirements as is appreciated from the above references, as well as those discussed below.

WO 03/011809 to BP Chemicals, Feb. 2, 2003, describes a process for separating secondary butanol impurity from ethyl acetate by feeding the impure ethyl acetate to a distillation column operating at a pressure of less than 1 bar absolute. This provides (1) a stream comprising ethyl acetate as a major component and (2) a residue or a second stream comprising at least some secondary butanol from ethyl acetate. The process can be applied to purifying ethyl acetate derived from (a) catalytic reaction of ethylene with acetic acid followed by (b) a hydrogenation step. The 2-butanone impurity produced in step (a) is difficult to separate from ethyl acetate, and step (b) converts it to secondary butanol, which can be separated by reduced pressure fractionation.

A process for removing at least one compound selected from acetic acid, acetate esters and aldehydes from a gaseous fraction additionally containing carbon dioxide is described in U.S. Pat. No. 6,663,692 entitled "Process for Purifying Carbon Dioxide-Containing Gas Streams" of de Poitiers et al. The process includes the steps of scrubbing in a scrubber at least part of the gaseous fraction with water and acetic acid to remove the acetic acid, acetate esters and/or aldehydes and removing carbon dioxide from the scrubbed product by absorption in aqueous potassium carbonate. The process may be used to remove acetate esters such as vinyl acetate and ethyl acetate and aldehydes such as acetaldehyde. The process may be employed in the manufacture of vinyl acetate by the reaction of ethylene, acetic acid and an oxygen-containing gas in the presence of a catalyst, or in the catalytic oxidation of (a) ethane and/or (b) ethylene to produce respectively (a) acetic acid and/or ethylene and (b) acetic acid.

SUMMARY OF THE INVENTION

The present invention provides numerous advantages over the prior art. For one, overall throughput is increased for given capital investment. For another, purification costs are reduced by withdrawing a vinyl acetate stream enriched in ethyl acetate and converting the vinyl acetate to ethyl acetate rather than removing the ethyl acetate. Still another advantage of the invention is that the purge rate (raw material which is eventually discarded) is reduced with respect to conventional processing.

A method of co-producing vinyl acetate and ethyl acetate in accordance with the invention includes: (a) reacting ethylene, acetic acid and oxygen to form vinyl acetate and at least a minor amount of ethyl acetate; (b) providing a crude product stream containing the vinyl acetate and ethyl acetate of step (a) and acetic acid to a distillation tower; (c) separating the crude product stream into: (i) a vinyl acetate product stream enriched in vinyl acetate with respect to the crude product stream; (ii) an acid recycle stream enriched in acetic acid with respect to the crude product stream; (iii) a mixed sidestream containing vinyl acetate and ethyl acetate, the mixed sidestream being enriched in ethyl acetate with respect to the vinyl acetate product stream; and (d) hydrogenating vinyl acetate in the mixed sidestream to provide an ethyl acetate product stream. Preferably, vinyl acetate in the mixed sidestream is catalytically hydrogenated using a Raney Nickel catalyst or a palladium/carbon catalyst. Hydrogenation may be carried out in a CSTR or in a fixed bed reactor, such as a trickle-bed reactor. The process typically further includes the step of distilling the ethyl acetate product stream, preferably using a single distillation tower.

Generally, the vinyl acetate product stream of step (c) is substantially an azeotropic mixture of water and vinyl acetate and it preferably contains less than about 0.025 weight percent ethyl acetate based on the weight of ethyl acetate and vinyl acetate. The ratio of mass flow rates of vinyl acetate in the product stream to the flow rate in the mixed sidestream is typically from about 10:1 to about 2:1 and may be from about 6:1 to about 3:1 in many cases. The step of reacting ethylene, acetic acid and oxygen may be carried out in the liquid phase; but is perhaps more typically carried out in the vapor phase with a palladium catalyst or with a palladium/gold catalyst.

An apparatus for co-producing vinyl acetate and ethyl acetate in accordance with the invention includes: (a) a reactor for reacting ethylene, acetic acid and oxygen to form vinyl acetate and at least a minor amount of ethyl acetate; (b) means for providing a crude product stream containing the vinyl acetate and ethyl acetate of step (a) and acetic acid to a distillation tower; (c) a distillation tower adapted for separating the crude product stream into: (i) a vinyl acetate product stream enriched in vinyl acetate with respect to the crude product stream; (ii) an acid recycle stream enriched in acetic acid with respect to the crude product stream; (iii) a mixed sidestream containing vinyl acetate and ethyl acetate, the mixed sidestream being enriched in ethyl acetate with respect to the vinyl acetate product stream; and (d) means for hydrogenating vinyl acetate in the mixed sidestream to provide an ethyl acetate product stream. The means for hydrogenating the mixed sidestream includes a CSTR reactor provided with a catalyst selected from Raney Nickel catalysts and palladium/carbon hydrogenation catalysts.

DETAILED DESCRIPTION

The invention is described in detail below with reference to the drawings for purposes of exemplification and illustration only. Modifications within the spirit and scope of the present invention, set forth in the appended claims, will be readily apparent to those of skill in the art.

Unless more specifically defined, terminology as used herein is given its ordinary meaning. Percent, for example, refers to weight percent. Throughout the specification and claims, the following abbreviations are sometimes used:

| | |
|---|---|
| "AcH"— | Acetaldehyde; |
| "CSTR"— | Continuous stirred tank reactor; |
| "DMK"— | Dimethyl ketone; |
| "EtAc"— | Ethyl acetate; |
| "HOAc"— | Acetifc acid; |
| "I-PrAc"— | Isopropyl acetate; |
| "I-PrOH— | Isopropyl alcohol; |
| "pBQ"— | Para-benzoquinone; |
| "Pd/C"— | Palladium on carbon catalyst; |
| "RaNi" or "Raney Ni"— | Raney nickel catalyst: |
| "STY"— | Space/time yield; and |
| "VAM"— | Vinyl acetate. |

Vinyl acetate monomer is used in both a monomer form and a polymerized form. In the monomer form, vinyl acetate monomer has wide applicability in manufacture of synthetic adhesives, acrylic fiber, polymers and so forth. Alternatively, emulsions of vinyl acetate in polymer form include emulsions containing polyvinyl acetate, polyvinyl alcohol and ethyl vinyl acetate. These emulsions in turn are used in various industries like wood, paper, rubber and so on. Typical specifications of vinyl acetate monomer are as follows:

TABLE 1

Vinyl Acetate Specifications

| Characteristics | Specification | Unit |
|---|---|---|
| Boiling Point | 72 | ° C. |
| Melting Point | −93 | ° C. |
| Relative density | 0.9 | Water = 1 |
| Solubility in water | 2.5 | g/100 ml @ 20° C. |
| Vapor pressure | 11.7 | kPa @ 20° C. |
| Ethyl Acetate | <0.025 | wt. % |

Ethyl acetate is generally used for adhesives, paint, offset inks, polymerization media, synthetic resins, and the like. Typical specifications of ethyl acetate are as follows:

TABLE 2

Ethyl Acetate Specifications

| Characteristics | Specification | Unit | Test Method |
|---|---|---|---|
| Specific Gravity, 20/20° C. | 0.900~0.903 | g/cm³ | ASTM D 1298 |
| Distillation - Initial Boiling Point | 75 | ° C. | ASTM D 1078 |
| Distillation - Dry Point | 78 | ° C. | ASTM D 1078 |
| Acidity | Max. 0.01 | wt % | ASTM D 1613 |
| Purity | Min. 99.5 | wt % | G.C. |
| Water Content | Max. 0.5 | wt % | ASTM D 1364 |
| Ethanol | Max. 0.1 | wt % | G.C. |

Ethyl acetate is a side-product impurity common to vinyl acetate manufacturing that requires removal in a purification system. Vapor phase, palladium catalyzed vinyl acetate systems typically produce ethyl acetate at a 1000 or more ppm level, which must be reduced to <250 ppm in the vinyl acetate product. This reduction is conventionally achieved by distillation to concentrate the ethyl acetate in a waste stream. This waste stream (which is typically discarded) is currently minimized at high operating and capital cost to reduce waste of raw materials.

In accordance with the present invention throughput is improved because there is diverted a larger mass flow of vinyl acetate with ethyl acetate in a sidestream which is provided to a hydrogenation reactor to convert vinyl acetate in the stream to ethyl acetate. Synergy derived advantages in efficiency, product yield, energy consumption and capital costs result. The co-production process reduces azeotropic tower rectification requirements and energy usage. One benefit of the inventive process is that it enables regional EtAc production directly tied to ethylene raw material pricing without spending capital for building a dedicated ethylene acetoxylation based EtAc production unit that is approximately 1.8-2.0 times higher in cost than an EtOH esterification unit with the same production capacity.

As previously explained, the production of a vinyl acetate monomer is well known. The method comprises the combining of acetic acid (I) and ethylene (II) in the presence of oxygen to produce the vinyl acetic monomer (III):

In accordance with the invention, hydrogenation of vinyl acetate monomer in a sidestream of vinyl acetate/ethyl acetate yields relatively pure ethyl acetate (IV):

Various hydrogenation methods may be used, for example a single stage continuous stirred tank reactor (CSTR) or a trickle bed type reactor. With regard to catalysts, numerous options are available including Raney Ni and Pd/C type catalysts. Both catalysts are effective. The use of the nickel catalyst in high acid steams that could potentially come from azeotropic tower side stream locations near the base of the tower is not recommended. The Pd/C hydrogenation is substantially equivalent to Raney Ni. However, the nickel catalyst is generally a lower cost catalyst system that is available for hydrogenation of purer vinyl acetate monomer (i.e. one with lower HOAc content).

Alternatively, hydrogenation of vinyl acetate may be performed with cyclometallated transition metal catalysts is described in U.S. Pat. No. 4,645,849 entitled "Hydrogenation of Unsaturated Hydrocarbons with Cyclometallated Transition Metal Catalysts" of Lewis. This method for hydrogenating unsaturated hydrocarbons comprises reacting an unsaturated hydrocarbon with hydrogen in a solution of cyclometallated complex catalyst at a temperature above about 20° C., the unsaturated hydrocarbon comprises less than about 50 mole percent of the reaction mixture and is selected from aliphatic and cyclic olefins and alkynes of from 2 to 10 carbon atoms, aromatic hydrocarbons of from 8 to 18 carbon atoms having olefinic or alkyne functionality within hydrocarbon radicals of from 2 to 4 carbon atoms and siloxanes of from 1 to 10 —(Si—O)— units having olefinic or alkyne functionality within hydrocarbon radicals of from 2 to 4 carbon atoms, subject to the proviso that the unsaturated hydrocarbons contain no acidic functional groups, and the cyclometallated complex catalysts having a 4-6 membered ring with a chemically combined unit of the formula:

wherein M is a transition metal, L is a ligand selected from the group consisting of phosphorus, nitrogen, arsenic, oxygen and sulfur and C is a covalently bonded carbon atom of a hydrocarbon species having at least 6 carbon atoms.

The ring structure is typically of the formulas:

where Z is nitrogen or carbon.

Preferably, the hydrogenation is effective to convert all or nearly all of the vinyl acetate so that the hydrogenated stream can be purified with a single distillation step.

The following description and examples illustrate preferred methods and apparatus of the invention. These examples are illustrative only and do not limit the scope of the invention. All percentages are by weight, unless otherwise indicated.

Figure 1:
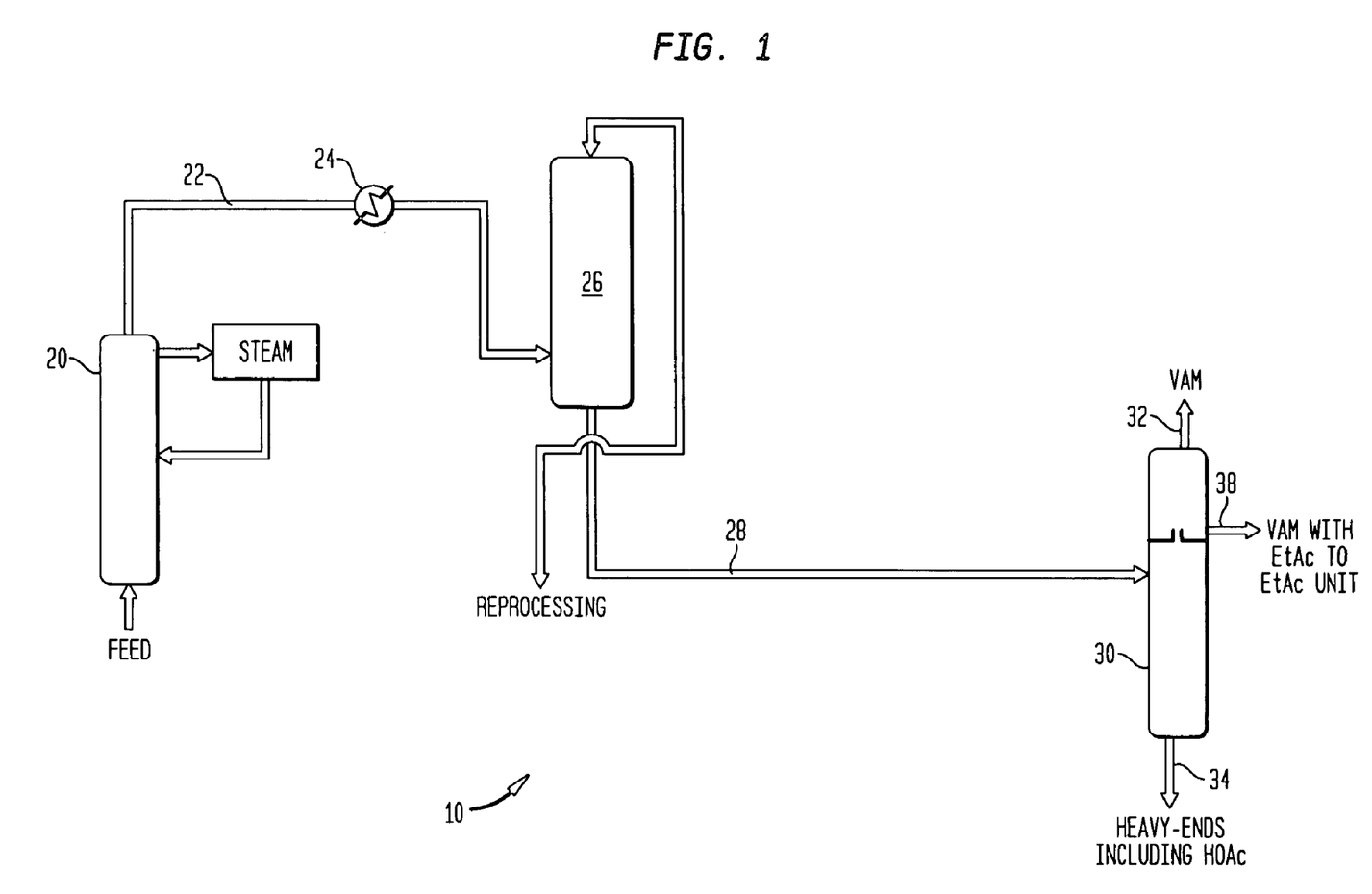
FIG. 1 is a flow diagram of a vinyl acetate production unit including an azeotropic tower having a vinyl acetate monomer output stream and an ethyl acetate/vinyl acetate output sidestream according to a preferred embodiment of the present invention.

There is shown schematically in FIG. 1, a typical apparatus 10 for manufacturing vinyl acetate by way of a vapor phase process. A catalytic reactor 20 reacts acetic acid, ethylene and oxygen to produce vinyl acetate, which exits the reactor to a product stream 22. Stream 22 is cooled in an effluent cooler 24 which feeds a vinyl acetate absorber column 26. Crude product stream 28 from the bottom of the absorber feeds an azeotrope tower 30. Ancillary streams are omitted for purposes of brevity, but may be configured as seen in the U.S. Pat. No. 6,420,595 noted above.

Crude stream 28 consists mainly of vinyl acetate, acetic acid and water, but also contains significant amounts of ethyl acetate.

Tower 30 separates vinyl acetate, water and other light components from acetic acid. Vinyl acetate along with water approaching the vinyl acetate-water azeotrope is taken overhead as vinyl acetate product stream 32. The tower bottoms stream 34 is generally from 70% to 90% acetic acid, which is returned to the system.

A sidedraw stream 38 is located at an elevation higher than the fed and is fed forward for hydrogenation. Stream 38 contains VAM, H$_2$O, ethyl acetate and acetic acid, as further discussed below.

Sidestream 38 is fed forward to a reactor 40 (FIG. 2) which may be a CSTR reactor or a fixed bed reactor, together with a hydrogen stream 42. Reactor 42 optionally includes stirring means if hydrogenation is carried out in solution. Hydrogenation of the VAM fed by way of stream 38 is carried out in reactor 40 and the product, crude ethyl acetate, is fed forward at 44 to a distillation tower 46 which may be a divided or split tower as shown. Finished ethyl acetate is withdrawn at 48, while acetic acid is recycled via line 50. Overhead from tower 46 is decanted at 52, providing reflux to the column while minor components are purged or vented.

The present invention compares very favorably with conventional processing in terms of raw material usage, capital, and energy costs. Consider the following. Oxidative acetoxylation VAM production units typically produce ~0.0016 tons EtAc per ton of VAM as a reaction by-product. This by-product is an impurity that must be separated from VAM for generation of sales grade product (<0.025 wt % EtAc). EtAc, which can be concentrated as a "bulge" in the azeo-column, is then typically purged via a liquid sidestream draw-off below the feed tray; note the '595 Hallinan patent referenced above. The purge sidestream generally contains VAM, HOAc, $H_2O$, EtAc, and AcH in various ratios depending upon the number of trays in the azeo-column. The sidestream, for example, may contain ~17.5% VAM, ~9% $H_2O$, ~61% HOAc, ~0.6% AcH and the EtAc is concentrated up to ~15.5%. The VAM unit eventually must dispose of the EtAc impurity resulting in an efficiency loss plus the energy and equipment costs necessary to concentrate the EtAc. If the 0.16 wt % EtAc formed in the reaction step must be attenuated to a specification level of at least 0.025 wt %, then this 0.135 wt % delta EtAc if concentrated to, for example, 15.5 wt % still results in a waste stream that is roughly 0.135/0.155=0.87% (w/w) of the VAM production rate. Removal of all the EtAc would require a purge rate of ~1.34%.

With the present invention, production is integrated such that combined VAM and EtAc manufacturing units may use, for example, one-fourth of the VAM capacity could eliminate the current practice of using an azeotrope tower sidestream waste stream to control EtAc as an impurity in Specification VAM. A concerted VAM/EtAc co-production unit would not only eliminate this EtAc "bulge" waste stream, but it would also reduce the need for VAM catalysts and reactor operating conditions that were designed to minimize EtAc formation.

Figure 2:
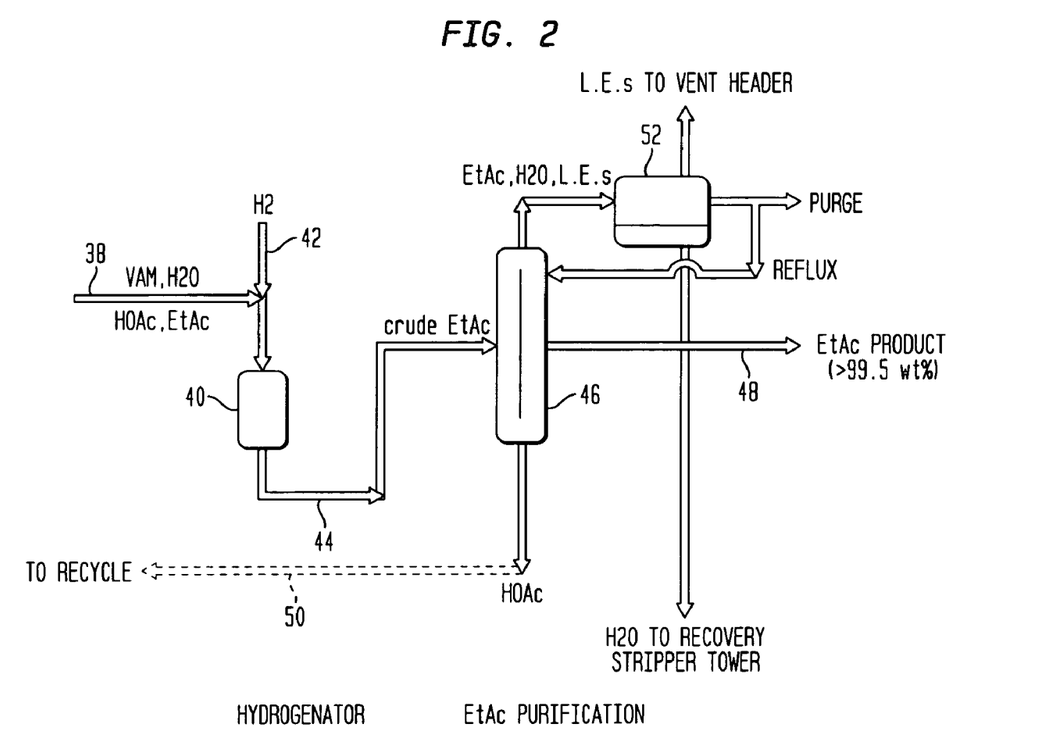
FIG. 2 is a flow diagram for hydrogenation of the ethyl acetate/vinyl acetate stream output of FIG. 1 according to one preferred embodiment of the present invention.

Referring to FIGS. 1 and 2 above, a high volume liquid sidestream (i.e., ~25% of the VAM unit production rate) taken at a tray slightly above the azeo tower feed tray would continue to concentrate HOAc in a high volume residue recycle stream and a low acid, low EtAc content overhead VAM stream (feed to VAM purification). The proposed liquid sidestream should contain primarily VAM, but also be contains $H_2O$, a small amount of HOAc, and a sufficient quantity of EtAc to provide a sufficient purge of this VAM impurity to maintain specification VAM production. The liquid sidestream may have a composition as follows: ~94.3 wt % VAM, ~5.28 wt % $H_2O$, 0.14 wt % HOAc, and ~0.05 wt % EtAc. Hydrogenation of this stream produces a crude EtAc product (>94% assay) containing HOAc, water, and a low concentration of light-ends (some from the crude VAM and some produced by the hydrogenation step).

The invention is further appreciated by reference to the following examples, wherein materials, procedures and results are summarized in Table 3 and further described below.

EXAMPLES

Hydrogenation of VAM to EtAc

General Procedure: A 300 ml autoclave with stirrer was configured as a batch hydrogenation reactor for testing both Raney Nickel and Pd/C hydrogenation catalysts with either para-benzoquinone inhibited VAM or a synthetic sidestream VAM mixture. Hydrogen uptake was measured by pressure changes in a ~2500 ml $H_2$ reservoir used to feed the reactor $H_2$ through a pressure control valve used to maintain a constant reaction pressure set-point. Temperature control was generally accomplished by the flow of chilled water through an internal autoclave-cooling coil after initiation of the reaction by starting the stirrer. Reaction samples were collected from the reactor via a sintered stainless steel filtering element placed in the autoclave. Reaction charges, conditions, experimental data, and reactor sample analyses were included in Table 3 (attached). Reaction times (minutes) listed in Table 3 refer to the $H_2$ uptake time. A preliminary run was made without addition of $H_2$ to determine the compatibility of RaNi with HOAc containing reaction charges. The RaNi used in the experiments was Grace Raney 4310 w/Mo stored under water. RaNi (6.4 g, as dry weight) was rinsed three times with isopropanol and again with HOAc in a 125 ml flask, and then was transferred to the autoclave with additional HOAc. VAM inhibited with pBQ (500 ppm) was added to the autoclave, then the autoclave was pressurized with $N_2$ to ~115 psig, and heated to ~72° C., with stirring (~1500 rpm) for ~2 hours. The product sample was green in color and was analyzed to contain 3522 ppm Ni, 0.18 wt % $H_2O$, 77.22 wt % VAM, 0.39 wt % EtAc, 21.67 wt % HOAc. The preliminary experiment was repeated using the isopropanol rinse, but with no HOAc rinsing or addition of HOAc to the reactor. The product from this test was clear with no color and was analyzed to contain 0.2 wt % $H_2O$, 24.22 wt % isopropanol, and 74.75 wt % VAM. No compatibility problems were observed with isopropanol, but the presence of HOAc when using RaNi resulted in unacceptable nickel solubility losses.

Raney Ni Catalyzed Hydrogenation

Examples 1-6

Six batch autoclave RaNi catalyzed VAM hydrogenation runs were conducted. The first experiment (Run-173) was made using the reactor charge from Run-169 (above) at a pressure of 110 psig, stirrer rate=~1500 rpm, target temperature=50° C. The peak temperature from the exothermic reaction was 85° C.

Example 2 was a repeat of the previous experiment with a fresh charge of RaNi (washed only with I-PrOH) conducted at a pressure of 105+/−2 psig, target temperature=50° C. (peak=61° C.), and a ~1500 rpm stirrer rate.

Example 3 was also a repeat using another fresh charge of catalyst. The peak temperature was 54° C. and the pressure was controlled in a range of 100 to 105 psig at a stirrer rate of ~1500 rpm.

The reactor pressure was increased to ~204 psig for Example 4. The reaction temperature target was 50, but briefly peaked at 89° C. about three minutes after the stirrer (~1500 rpm) was started. The RaNi charge solvent exchange for Example 4 was attempted with just VAM to rinse off water from the catalyst, but the water reacted with the VAM resulting in solids sticking to the 125 ml flask used for the rinsing steps, the solution developed a green color, and gas evolution was noted. A new catalyst charge was rinsed using the I-PrOH procedure. Also, a new VAM feed solution was prepared using VAM from a 55 gallon drum with ~52 ppm para benzoquinone.

Example 5 used a fresh charge of RaNi that was first rinsed with isopropanol followed by VAM rinses to remove most of the I-PrOH. The reaction temperature was maintained at <51° C. throughout the run, the pressure was regulated at 103+/−3 psig, and the stirrer rate was ~1500 rpm. The double solvent exchange method resulted in a low water "neat" VAM hydrogenation run.

Example 6 was a repeat of the Example 5 using the Ra/Ni double solvent exchange method, a reaction temperature of ~50° C. and a reaction pressure of ~101 psig. However, the stirrer rate was decreased by half to ~750 rpm. The exotherm was noticeably less pronounced at the lower stirrer rate and the $H_2$ uptake rate was essentially cut in half.

Palladium on Carbon Catalyzed Hydrogenation

Examples 7-9

Three experiments were conducted using PMC 5% Pd on a carbon support. The Pd/C contained 58.13 wt % $H_2O$. The catalyst charges were adjusted for water content and were reported in Table I on a "dry" basis.

Example 7 utilized HOAc, H2O, EtAc, VAM, pBQ and the Pd/C catalyst to approximate hydrogenation of a VAM azeo tower sidestream. The run was made at a pressure of 107+/−3 psig at a temperature of about 50° C. during the first 30 minutes. The hydrogen feed vessel showed no drop in pressure after about 4 minutes reaction time even with a ~10° C. increase in the reaction temperature for the last 35 minutes of reaction time. The stirring rate was ~1000 throughout the run.

Example 8 was a repeat of the previous Pd/C catalyzed experiment, Example 7, including an increase in reaction temperature from the initial target=50° C. to 60° C. during the last 30 minutes. The stirrer rate was ~1000 rpm during the run and the pressure was maintained at 103+/−3 psig. No $H_2$ uptake was observed after the initial 6 minutes of reaction time.

For example 9, the reaction vessel was charged with only Pd/C catalyst and VAM inhibited with 50 ppm pBQ. Operation was at 106+/−3 psig pressure, initial target temperature ~50° C. during the first 30 minutes and 60° C. during the last 30 minutes at a stirrer rate ~1000 rpm. The exotherm for this neat VAM run resulted in a maximum temperature of 59° C. during the first ten minutes. Hydrogen uptake stopped after ~16 minutes reaction time.

Figure 3:
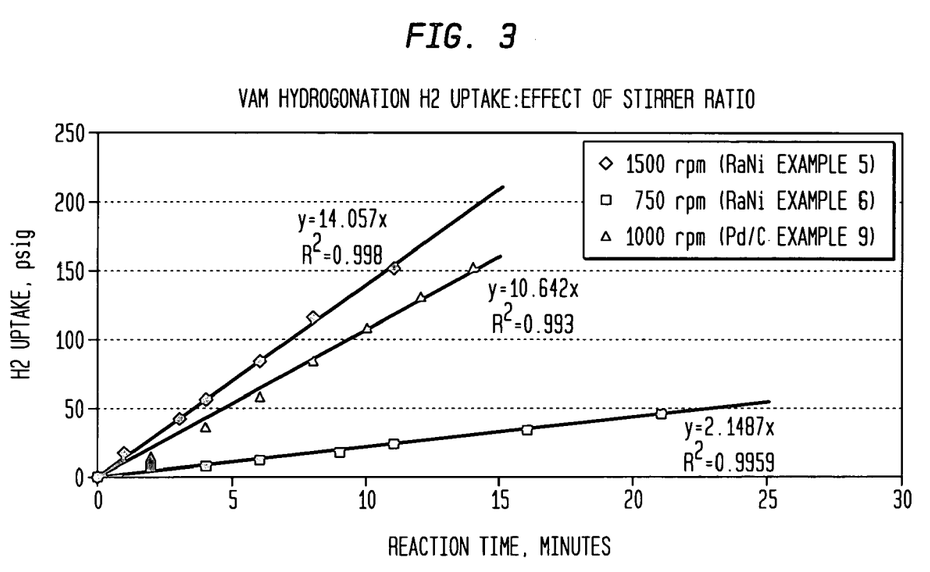
FIG. 3 is a plot of hydrogen uptake during vinyl acetate hydrogenation for different conditions, catalysts and stirrer speeds.

Representative results appear in FIG. 3.

As will be appreciated from Table 3 and FIG. 3, the selectivity of VAM hydrogenation to EtAc was good for all of the experimental runs. Also, the autoclave stirrer rate made a noticeable difference in $H_2$ uptake. No $H_2$ uptake was observed unless the stirrer was started. The stirrer start time was used as the reaction time=zero for all of the heterogeneous catalyzed autoclave experiments. Although a direct comparison of initial $H_2$ uptake rates between RaNi and Pd/C catalyzed runs was not made, FIG. 3 shows plots for three of the VAM hydrogenation runs at three different autoclave stirrer rates. The RaNi catalyzed runs were made at roughly a 3% (w/w) catalyst concentration. The 5% Pd/C experiments were made at a lower catalyst concentration, i.e., <1.5% (w/w), which from a metal loading perspective lowered the catalyst level to <0.075% Pd. The reaction completion (as measured by the $H_2$ take-up) were comparable between the Ni and Pd catalysts as were the reaction rates, e.g., ~0.065+/−0.004 gmole/minute for the VAM hydrogenation runs conducted without HOAc. The STY calculated from the $H_2$ uptake rates for all of the runs (both catalysts) was ~30+/−2 gmole/Liter/hour (excluding the low stirrer rate and high pressure runs in the average). The VAM hydrogenation molar conversions were high (>95%) for most of the experimental runs (excluding the first RaNi and Pd/C runs). The VAM concentrations varied from 0.02-1.12 wt % in reactor product samples (excluding the initial experimental run)

Impurities such as HOAc and AcH are consistent with VAM hydrolysis and EtOH can be formed by the hydrogenation of the AcH. Ethylene and HOAc can be generated from VAM. Ethylene can be a source of butylenes and hydrogenation of ethylene to ethane and butene to butane would be the expected subsequent products.

The liquid phase, heterogeneous catalyzed hydrogenation of VAM and mixtures containing VAM was thus demonstrated with high conversions (>95%) at good space-time yield (STY) reaction rates using mild hydrogenation conditions (i.e., 100-200 psig, <90° C.).

Both Raney nickel (RaNi) and palladium on carbon (Pd/C) heterogeneous catalysts were tested with Specification Grade VAM, and the experimental results were fairly equivalent. Vinyl acetate hydrogenation in solutions containing acetic acid concentrations of 60+/−5 wt % were also tested using Pd/C catalyst with good results. However, the RaNi catalyst system was found to be applicable to only catalyzing hydrogenation reactions of VAM with low HOAc content due to the high solubility of nickel in HOAc, which resulted in excessive RaNi catalyst losses.

By-product impurities, such as, ethane, butane, and butane were produced in higher quantities using the RaNi catalyst. Ethane formation was assumed to be via hydrogenation of ethylene and was also formed in the low-acetic acid Pd/C catalyst experiment. Acetone formation during RaNi runs was attributed to dehydrogenation of isopropanol used to rinse water from the RaNi reaction charge.

Initial $H_2$ uptake rates used for RaNi experiments were ~43 gmoles/L/hr at 100 psig (system pressure), ~50° C., and ~1500 rpm stirrer rates. Doubling the reactor operating pressure to 200 psig showed an increased $H_2$ uptake rate that was at least three times the uptake rate observed for batch reactions conducted at 100 psig. Autoclave stirrer rates were varied from ~750 to 1500 rpm and were also found to have a directly relationship with the $H_2$ uptake rate. Raney nickel would be the preferred catalyst system for a "stand-alone" EtAc production unit that would be fed high assay (essentially Specification Grade) VAM.

Synergistic co-production of VAM and EtAc of the invention is perhaps most applicable to construction of new production units to take advantage of the economy-of-scale capital savings associated with building a larger VAM unit necessary to supply VAM sales and to supply EtAc feedstock. Other advantages of VAM/EtAc co-production are: 1) the elimination of the current azeotrope tower waste stream (~1% of VAM production) required for EtAc impurity control and, 2) the need to used catalysts and VAM reactor conditions that are designed to minimize EtAc production.

TABLE 3

Hydrogenation Run Conditions and Results

| Ex. | Catalyst, g | 50 pBQ VAM, g | Solvent isoPrAc | psig delta | P psig | T, °C. avg | T, °C. max | Time min | Stir rpm |
|---|---|---|---|---|---|---|---|---|---|
| | RaNi | | | | | | | | |
| 1a | 4.142 | 100.02 | 36.5074 | 90 | 110 | 50 | 85 | 17 | 1510 |
| 1b | | 100.2 | 36.5074 | 34 | 110 | 50 | 51 | 101 | |
| 2a | 4.0326 | 100.18 | 36.9674 | 124 163 | 105 | 50 | 61 | 23 | 1500 |
| 2b | | 100.18 | 36.9674 | 2 | 164 | 51 | 51 | 7 | |
| 3 | 3.9104 | 100.1 | 37.33 | 165 156 | 105 | 52 | 54 | 13 | 1520 |
| 4 | 3.8249 | 100.47 | 34.065 | 162 | 204 | 59.4 | 89 | 6 | 1480 |
| 5 | 3.2139 | 115.136 | VAMrinse 0 | 198 | 102 | 50 | 51 | 26 | 1500 |
| 6 | 3.3116 | 119.4 | VAMrinse 0 | 184 | 101 | 44.1 | 50 | 90 | 750 |
| | Pd/C | | Mixture* | | | | | | |
| 7 | 1.15 | 20.15 | 78.97 | 30 | 104 | 36 | 50 | 4 | 1060 |
| 8 | 1.15 | 20.2154 | 78.86 | 32 | 100 | 38.75 | 47 | 6 | 1010 |
| 9 | 1.152 | 100.08 | 0 | 156 | 103 | 54.25 | 59 | 16 | 1025 |

| Ex. | Catalyst, g | weight percent analytical values | | | | parts-per-million analytical values (G.C.) | | | |
|---|---|---|---|---|---|---|---|---|---|
| | | H2O | I-PrOH | VAM | EtAc | HOAc | EtOH | DMK | iPrAc | BuAc |
| | RaNi | | | | | | | | | |
| 1a | 4.142 | | | | | | | | | |
| 1b | | 0.31 | 24.6 | 12.19 | 55.36 | 5.73 | 572 | 421 | 2505 | 11 |
| 2a | 4.0326 | 0.15 | 25.51 | 3.14 | 66.84 | 1.49 | 154 | 163 | 395 | 72 |
| 2b | | 0.16 | 25.52 | 0.02 | 69.95 | 1.6 | 176 | 151 | 341 | 74 |
| 3 | 3.9104 | 0.24 | 23.59 | 0.69 | 70.8 | 1.28 | 70 | 115 | 143 | 40 |
| 4 | 3.8249 | 0.12 | 26.24 | 0.9 | 73.52 | 1.59 | 36 | 126 | 38 | 68 |
| 5 | 3.2139 | 0.11 | | 0.97 | 100.2 | 1.03 | 35 | 46 | 55 | 52 |
| 6 | 3.3116 | 0.12 | | 1 | 102.4 | 2.07 | 27 | 188 | | 162 |
| | Pd/C | | | | | | | | | |
| 7 | 1.15 | 15.7 | | 0.53 | 30.22 | 54.82 | 1265 | 55 | | 81 |
| 8 | 1.15 | 15.4 | | 0.046 | 34.05 | 63.88 | 1136 | | 12 | 72 |
| 9 | 1.152 | 1.52 | | 1.12 | 102 | 0.22 | 22 | 29 | | 122 |

| Ex. | Catalyst, g | H2 psi/min | psig | EtAc, g | Conv. % | molar Gmole | EtAc Mole/L/hr |
|---|---|---|---|---|---|---|---|
| | RaNi | | | | | | |
| 1a | 4.142 | 5.294 | | | | | 16.449 |
| 1b | | | 124 | 75.681 | 73.814 | 0.860 | |
| | | | | 75.680 | | | |
| 2a | 4.0326 | 7.087 | | 91.669 | 89.425 | | 21.920 |
| 2b | | | 165 | 95.935 | 93.586 | 1.090 | |
| | | | | 95.930 | | | |
| 3 | 3.9104 | 12.000 | 156 | 97.300 | 94.994 | 1.106 | 37.040 |
| 4 | 3.8249 | 27.000 | 162 | 98.910 | 96.210 | 1.124 | 85.133 |
| 5 | 3.2139 | 7.615 | 198 | 115.332 | 97.893 | 1.311 | 28.058 |
| 6 | 3.3116 | 2.044 | 184 | 122.25 | 100.063 | 1.389 | 7.263 |
| | Pd/C | | | | | | |
| 7 | 1.15 | 7.500 | 30 | 16.774 | 81.354 | 0.191 | 32.097 |
| 8 | 1.15 | 5.333 | 32 | 20.495 | 99.080 | 0.233 | 22.835 |
| 9 | 1.152 | 9.750 | 156 | 102.04 | 99.643 | 1.160 | 41.326 |

*HOAc, H20, EtAc charged to reactor

| Run | HOAc | H2O | EtAc | total |
|---|---|---|---|---|
| 199 | 52.35 | 13.44 | 13.18 | 78.97 |
| 207 | 52.13 | 13.49 | 13.24 | 78.86 |

While the invention has been described in connection with several examples, modifications to those examples within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary.

What is claimed is:

1. A method of co-producing vinyl acetate and ethyl acetate comprising: (a) reacting ethylene, acetic acid and oxygen to form vinyl acetate and at least a minor amount of ethyl acetate; (b) providing a crude product stream containing the vinyl acetate and ethyl acetate of step (a) and acetic acid to a distillation tower; (c) separating the crude product stream into: (i) a vinyl acetate product stream enriched in vinyl acetate with respect to the crude product stream; (ii) an acid recycle stream enriched in acetic acid with respect to the crude product stream; (iii) a mixed sidestream containing vinyl acetate and ethyl acetate, the mixed sidestream being enriched in ethyl acetate with respect to the vinyl acetate product stream; and (d) hydrogenating vinyl acetate in the mixed sidestream to provide an ethyl acetate product stream, wherein the vinyl acetate in the mixed sidestream is catalytically hydrogenated.

2. The method according to claim 1, wherein vinyl acetate in the mixed sidestream is catalytically hydrogenated using a Raney Nickel catalyst.

3. The method according to claim 1, wherein vinyl acetate in the mixed sidestream is catalytically hydrogenated using a palladium/carbon catalyst.

4. The method according to claim 1, wherein the step of hydrogenating vinyl acetate in the mixed sidestream is carried out in a CSTR.

5. The method according to claim 1, wherein the step of hydrogenating vinyl acetate in the mixed sidestream is carried out in a fixed bed reactor.

6. The method according to claim 1, further comprising the step of distilling the ethyl acetate product stream.

7. The method according to claim 6, wherein the step of distilling the ethyl acetate product stream is carried out using a single distillation tower.

8. The method according to claim 1, wherein the vinyl acetate product stream of step (c) is substantially an azeotropic mixture of water and vinyl acetate.

9. The method according to claim 1, wherein the vinyl acetate product stream contains less than about 0.025 weight percent ethyl acetate.

10. A method of co-producing vinyl acetate and ethyl acetate comprising: (a) reacting ethylene, acetic acid and oxygen to form vinyl acetate and at least a minor amount of ethyl acetate; (b) providing a crude product stream containing the vinyl acetate and ethyl acetate of step (a) and acetic acid to a distillation tower; (c) separating the crude product stream into: (i) a vinyl acetate product stream enriched in vinyl acetate with respect to the crude product stream; (ii) an acid recycle stream enriched in acetic acid with respect to the crude product stream; (iii) a mixed sidestream containing vinyl acetate and ethyl acetate, the mixed sidestream being enriched in ethyl acetate with respect to the vinyl acetate product stream; and (d) hydrogenating vinyl acetate in the mixed sidestream to provide an ethyl acetate product stream, wherein the ratio of mass flow rates of vinyl acetate in the product stream to the flow rate in the mixed sidestream is from about 10:1 to about 2:1.

11. The method according to claim 10, wherein the ratio of mass flow rates of vinyl acetate in the product stream to the flow rate in the mixed sidestream is from about 6:1 to about 3:1.

12. The method according to claim 1, wherein the step of reacting ethylene, acetic acid and oxygen is carried out in the liquid phase.

13. The method according to claim 1, wherein the step of reacting ethylene, acetic acid and oxygen is carried out in the vapor phase.

14. The method according to claim 13, wherein the reaction between ethylene, acetic acid and oxygen to form vinyl acetate is catalyzed with a palladium catalyst.

15. The method according to claim 13, wherein the reaction between ethylene, acetic acid and oxygen to form vinyl acetate is catalyzed with a palladium/gold catalyst.

* * * * *